United States Patent
Aurich-Costa et al.

(10) Patent No.: US 8,877,441 B2
(45) Date of Patent: Nov. 4, 2014

(54) METHODS AND KITS FOR PERFORMING IN SITU HYBRIDIZATION

(71) Applicant: Cellay, Inc., Cambridge, MA (US)

(72) Inventors: Joan Aurich-Costa, Cambridge, MA (US); Elizabeth Ewen, Lynn, MA (US); Michael Gildea, Boston, MA (US)

(73) Assignee: Cellay, Inc., Cambridge, MA (US)

( * ) Notice: Subject to any disclaimer, the term of this patent is extended or adjusted under 35 U.S.C. 154(b) by 0 days.

(21) Appl. No.: 14/055,681

(22) Filed: Oct. 16, 2013

(65) Prior Publication Data

US 2014/0120535 A1 May 1, 2014

Related U.S. Application Data

(60) Provisional application No. 61/720,665, filed on Oct. 31, 2012.

(51) Int. Cl.
*C12Q 1/68* (2006.01)
*C12P 19/34* (2006.01)
*C12M 1/34* (2006.01)
*G01N 33/00* (2006.01)
*G01N 33/566* (2006.01)
*C07H 21/02* (2006.01)
*C07H 21/04* (2006.01)

(52) U.S. Cl.
CPC .................................. *C12Q 1/6841* (2013.01)
USPC ..... 435/6.1; 435/91.1; 435/287.1; 435/287.2; 436/94; 436/501; 536/23.1; 536/24.3; 536/24.33

(58) Field of Classification Search
USPC .................. 435/6.1, 6.11, 91.1, 283.1, 287.1, 435/287.2; 436/94, 501; 536/23.1, 24.3, 536/24.33
See application file for complete search history.

(56) References Cited

U.S. PATENT DOCUMENTS

| 5,310,650 | A | 5/1994 | McMahon et al. |
| 5,496,562 | A | 3/1996 | Burgoyne |
| 5,756,126 | A | 5/1998 | Burgoyne |
| 7,045,295 | B2 | 5/2006 | Loken |
| 8,088,576 | B2 | 1/2012 | Gumbrecht et al. |

FOREIGN PATENT DOCUMENTS

| EP | 1 795 612 A1 | 6/2007 |
| WO | WO 96/39813 A1 | 12/1996 |

OTHER PUBLICATIONS

International Search Report and Written Opinion in International Application No. PCT/US2013/065279, entitled "Methods and Kits for Performing In Situ Hybridization," date of mailing: Dec. 3, 2013.
Aurich-Costa, et al., "Oligo Fluorescence In Situ Hybridization (Oligo-FISH), a New Strategy for Enumerating Chromosomes in Interphase Nuclei," *Fertility and Sterility*, 88(1):586, Abstract O-231 (2007).
Quraishi, R., et al., "Apo E Genotyping from Blood Stored on Filter Paper," *Indian J. Med. Res.*, 135(3):318-321 (Mar. 2012).

*Primary Examiner* — Frank Lu
(74) *Attorney, Agent, or Firm* — Hamilton, Brook, Smith & Reynolds, P.C.

(57) ABSTRACT

The invention relates to methods and kits for performing in situ hybridization on a biological sample on a solid surface using nucleic acid probes that are embedded in or sorbed to a dry, fibrous matrix.

26 Claims, 2 Drawing Sheets
(2 of 2 Drawing Sheet(s) Filed in Color)

```
                        SEQUENCE LISTING

<160> NUMBER OF SEQ ID NOS: 19

<210> SEQ ID NO 1
<211> LENGTH: 27
<212> TYPE: DNA
<213> ORGANISM: Homo sapiens

<400> SEQUENCE: 1
ccagtcgaat ccattcgagt acatacc                                        27

<210> SEQ ID NO 2
<211> LENGTH: 27
<212> TYPE: DNA
<213> ORGANISM: Homo sapiens

<400> SEQUENCE: 2
ccttttgaat ccattccatt ggagtcc                                        27

<210> SEQ ID NO 3
<211> LENGTH: 30
<212> TYPE: DNA
<213> ORGANISM: Homo sapiens

<400> SEQUENCE: 3
attcattgca ttccgtttca tgaaattcga                                     30

<210> SEQ ID NO 4
<211> LENGTH: 30
<212> TYPE: DNA
<213> ORGANISM: Homo sapiens

<400> SEQUENCE: 4
ctgcatacaa tttcactcca ttcgttccca                                     30

<210> SEQ ID NO 5
<211> LENGTH: 30
<212> TYPE: DNA
<213> ORGANISM: Homo sapiens

<400> SEQUENCE: 5
tccattggag tcaattcctt tcgacaccca                                     30

<210> SEQ ID NO 6
<211> LENGTH: 30
<212> TYPE: DNA
```

```
<213> ORGANISM: Homo sapiens

<400> SEQUENCE: 6
ttgatcctat tttattaaat tgcattctat                                              30

<210> SEQ ID NO 7
<211> LENGTH: 30
<212> TYPE: DNA
<213> ORGANISM: Homo sapiens

<400> SEQUENCE: 7
gtgcgccctc aactaacagt gttgaagctt                                              30

<210> SEQ ID NO 8
<211> LENGTH: 30
<212> TYPE: DNA
<213> ORGANISM: Homo sapiens

<400> SEQUENCE: 8
gaaacgggat tgtcttcata taaactctag                                              30

<210> SEQ ID NO 9
<211> LENGTH: 30
<212> TYPE: DNA
<213> ORGANISM: Homo sapiens

<400> SEQUENCE: 9
gtatcttcca ataaaagcta gatagaagca                                              30

<210> SEQ ID NO 10
<211> LENGTH: 30
<212> TYPE: DNA
<213> ORGANISM: Homo sapiens

<400> SEQUENCE: 10
atgtcagaaa cttttcatg atgtatctac                                               30

<210> SEQ ID NO 11
<211> LENGTH: 30
<212> TYPE: DNA
<213> ORGANISM: Homo sapiens

<400> SEQUENCE: 11
tatgtgtgat gtgcgccctc aactaagagt                                              30

<210> SEQ ID NO 12
<211> LENGTH: 30
<212> TYPE: DNA
<213> ORGANISM: Homo sapiens

<400> SEQUENCE: 12
tctcagaagc ttcattggga tgtttcaatt                                              30

<210> SEQ ID NO 13
<211> LENGTH: 30
<212> TYPE: DNA
<213> ORGANISM: Homo sapiens

<400> SEQUENCE: 13
ggaatacggt gataaaggaa atatcttcca                                              30

<210> SEQ ID NO 14
<211> LENGTH: 30
```

```
<212> TYPE: DNA
<213> ORGANISM: Homo sapiens

<400> SEQUENCE: 14
tctttgtgtt gtgtgtactc atgtaacagt                                   30

<210> SEQ ID NO 15
<211> LENGTH: 30
<212> TYPE: DNA
<213> ORGANISM: Homo sapiens

<400> SEQUENCE: 15
tttctgccct acctggaagc ggacatttcg                                   30

<210> SEQ ID NO 16
<211> LENGTH: 30
<212> TYPE: DNA
<213> ORGANISM: Homo sapiens

<400> SEQUENCE: 16
ggttatcttc atataaaatc cagacaggag                                   30

<210> SEQ ID NO 17
<211> LENGTH: 30
<212> TYPE: DNA
<213> ORGANISM: Homo sapiens

<400> SEQUENCE: 17
cggcactacc tggaagtgga tatttcgagc                                   30

<210> SEQ ID NO 18
<211> LENGTH: 30
<212> TYPE: DNA
<213> ORGANISM: Homo sapiens

<400> SEQUENCE: 18
tctgcactac ctggaagagg ccatttcgag                                   30

<210> SEQ ID NO 19
<211> LENGTH: 30
<212> TYPE: DNA
<213> ORGANISM: Homo sapiens

<400> SEQUENCE: 19
cctacgggga gaaaggaaat atcttcaaat                                   30
```

METHODS AND KITS FOR PERFORMING IN SITU HYBRIDIZATION

RELATED APPLICATION

This application claims the benefit of U.S. Provisional Application No. 61/720,665, filed on Oct. 31, 2012. The entire teachings of the above application are incorporated herein by reference.

INCORPORATION BY REFERENCE OF MATERIAL IN ASCII TEXT FILE

This application incorporates by reference the Sequence Listing contained in the following ASCII text file being submitted concurrently herewith:
File name: 43731005001_FINALSEQUENCELISTING.TXT; created Sep. 26, 2013, 3 KB in size.

BACKGROUND OF THE INVENTION

In situ hybridization methods are widely used in the screening and testing of patients for medical conditions, particularly cancer. Successful in situ hybridization procedures depend, in part, on using hybridization probes at an appropriate, precisely measured concentration. Inaccurate results, including patient misdiagnoses, frequently occur when hybridization probes are used at an inappropriately high or low concentration.

Standard in situ hybridization procedures typically involve the preparation of a hybridization solution having a desired concentration of probe. To accomplish this, a precise amount of probe from a stock solution is measured and added to a particular volume of hybridization buffer using a micropipette. Errors in micropipetting, therefore, can result in hybridization solutions having suboptimal concentrations of probes, leading to high levels of background signal when probe concentrations are too high or insufficiently detectable signals when probe concentrations are too low.

Accordingly, there is a need to develop simplified and reliable in situ hybridization procedures that do not require the use of micropipettes to measure precise amounts of probe for the preparation of hybridization solutions having specific probe concentrations.

SUMMARY OF THE INVENTION

The present invention provides, in one embodiment, a method of determining whether a target nucleic acid is present in a biological sample on a solid surface. In this embodiment, the method comprises the steps of: a) contacting the sample on the solid surface with a dry fibrous matrix, wherein labeled nucleic acid probes for detecting the target nucleic acid are embedded in or sorbed to the matrix, and wherein the labeled nucleic acid probes comprise nucleotide sequences that are substantially complementary to one or more different nucleotide sequences in the target nucleic acid; b) hydrating the matrix to release the probes from the matrix; c) incubating the sample with the probes under stringent conditions sufficient to permit specific hybridization of the probes to the target nucleic acid if present in the sample; d) washing the sample to remove unhybridized probes and non-specifically hybridized probes; and e) determining whether the target nucleic acid is present in the sample by determining whether the labeled nucleic acid probes have hybridized to the sample.

In another embodiment, the invention relates to a method of enumerating chromosomes in a sample of cells immobilized on a slide. In this embodiment, the method comprises the steps of: a) overlaying the sample on the slide with a dry fibrous matrix comprising a glass fiber, wherein fluorescently-labeled synthetic DNA oligonucleotide probes for detecting one or more target chromosomal sequences in the sample are embedded in or sorbed to the matrix, and wherein the probes comprise nucleotide sequences that are substantially complementary to nucleotide sequences in the one or more target chromosomal sequences; b) hydrating the matrix with a hybridization buffer to release the probes from the matrix; c) incubating the sample with the probes under stringent conditions sufficient to permit specific hybridization of the probes to the target chromosomal sequences, if present in the sample; d) washing the sample to remove unhybridized probes and non-specifically hybridized probes; and e) enumerating chromosomes having the target chromosomal sequences in the sample by detecting labeled nucleic acid probes that have hybridized to the target chromosomal sequences in the sample.

In a further embodiment, the invention relates to a kit for detecting a target nucleic acid in a sample, comprising a dry fibrous matrix comprising labeled nucleic acid probes for detecting the target nucleic acid, wherein the labeled nucleic acid probes are embedded in or sorbed to the matrix, and wherein the labeled nucleic acid probes comprise nucleotide sequences that are substantially complementary to one or more nucleotide sequences in the target nucleic acid. In a particular embodiment, the kit further comprises a hydration buffer for releasing the probes from the matrix.

The in situ hybridization methods of the invention reduce the likelihood of micropipetting errors and ensure that an appropriate amount and concentration of probe is employed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Definitions

Figure 1A:
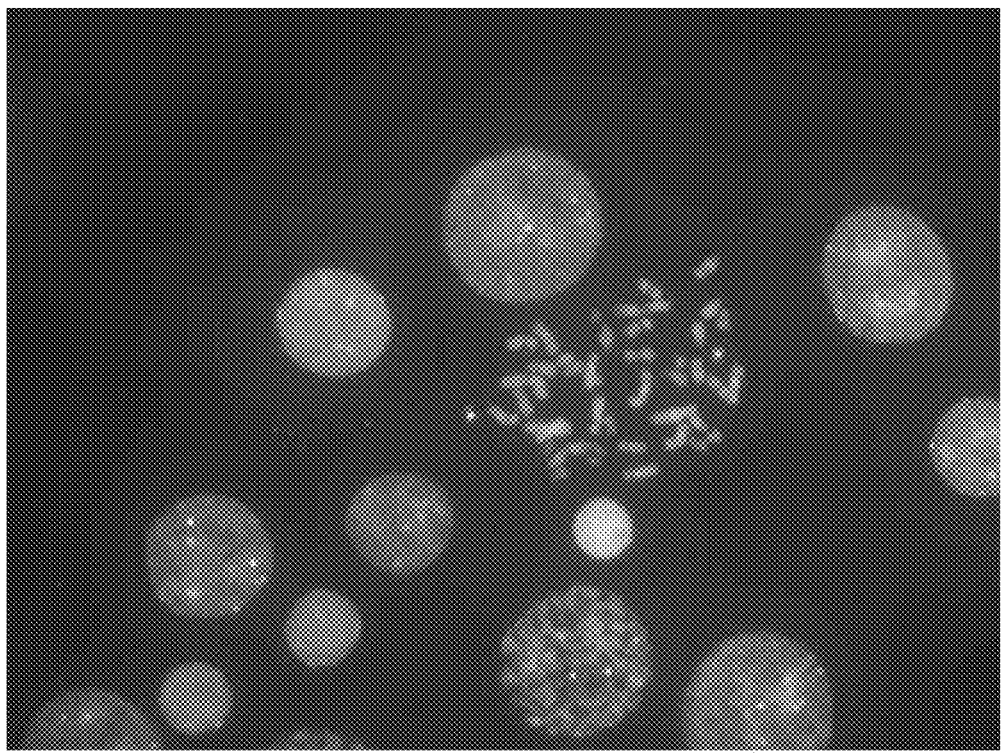
FIGS. 1A and 1B are images of human peripheral blood cells that have been hybridized at room temperature with an OligoFISH probe panel for chromosomes 3 (red), 6 (green), 7 (aqua) and 20 (gold) embedded on filter paper disks.

Unless defined otherwise, all technical and scientific terms used herein have the same meaning as commonly understood by one of ordinary skill in the art to which this invention pertains.

As used herein, the terms "room temperature" or "RT" refer to temperatures in the range of about 18 degrees Celsius to about 25 degrees Celsius.

The term "nucleotide" refers to naturally occurring ribonucleotide or deoxyribonucleotide monomers, as well as non-naturally occurring derivatives and analogs thereof. Accordingly, nucleotides can include, for example, nucleotides comprising naturally occurring bases (e.g., A, G, C, or T) and nucleotides comprising modified bases (e.g., 7-deazaguanosine, or inosine).

The term "sequence," in reference to a nucleic acid, refers to a contiguous series of nucleotides that are joined by covalent bonds (e.g., phosphodiester bonds).

The term "nucleic acid" refers to a polymer having multiple nucleotide monomers. A nucleic acid can be single- or double-stranded, and can be DNA (e.g., cDNA or genomic DNA), RNA, or hybrid polymers (e.g., DNA/RNA). Nucleic acids can be chemically or biochemically modified and/or can contain non-natural or derivatized nucleotide bases. Nucleic acid modifications include, for example, methylation, substitution of one or more of the naturally occurring nucleotides with an analog, internucleotide modifications such as uncharged linkages (e.g., methyl phosphonates, phosphotriesters, phosphoamidates, carbamates, and the like), charged linkages (e.g., phosphorothioates, phosphorodithioates, and the like), pendent moieties (e.g., polypeptides), intercalators (e.g., acridine, psoralen, and the like), chelators, alkylators, and modified linkages (e.g., alpha anomeric nucleic acids, and the like). Nucleic acids also include synthetic molecules that mimic nucleic acids in their ability to bind to a designated sequence via hydrogen bonding and other chemical interactions. Typically, the nucleotide monomers are linked via phosphodiester bonds, although synthetic forms of nucleic acids can comprise other linkages (e.g., peptide nucleic acids (also referred to herein as "PNAs"), such as described in Nielsen et al., Science 254, 1497-1500, 1991). Nucleic acids can also include, for example, conformationally restricted nucleic acids (e.g., "locked nucleic acids" or "LNAs," such as described in Nielsen et al., J. Biomol. Struct. Dyn. 17:175-91, 1999), morpholinos, glycol nucleic acids (GNA) and threose nucleic acids (TNA). "Nucleic acid" does not refer to any particular length of polymer and can, therefore, be of substantially any length, typically from about six (6) nucleotides to about $10^9$ nucleotides or larger. In the case of a double-stranded polymer, "nucleic acid" can refer to either or both strands.

The term "oligonucleotide" refers to a short nucleic acid, typically about 6 to about 100 nucleotide bases in length, joined by covalent linkages, such as phosphorus linkages (e.g., phosphodiester, alkyl and aryl-phosphonate, phosphorothioate, phosphotriester), and/or non-phosphorus linkages (e.g., peptide, sulfamate, and others).

The term "target nucleic acid" refers to a nucleic acid whose presence or absence in a sample is desired to be detected.

The term "target sequence" refers to a nucleotide sequence in a target nucleic acid that is capable of forming a hydrogen-bonded duplex with a complementary sequence (e.g., a substantially complementary sequence) on an oligonucleotide probe.

As used herein, "complementary" refers to sequence complementarity between two different nucleic acid strands or between two regions of the same nucleic acid strand. A first region of a nucleic acid is complementary to a second region of the same or a different nucleic acid if, when the two regions are arranged in an anti-parallel fashion, at least one nucleotide residue of the first region is capable of base pairing (i.e., hydrogen bonding) with a residue of the second region, thus forming a hydrogen-bonded duplex.

The term "substantially complementary" refers to two nucleic acid strands (e.g., a strand of a target nucleic acid and a complementary single-stranded oligonucleotide probe) that are capable of base pairing with one another to form a stable hydrogen-bonded duplex under stringent hybridization conditions, including the isothermal hybridization conditions described herein. In general, "substantially complementary" refers to two nucleic acids having at least 70%, for example, about 75%, 80%, 85%, 90%, 95%, 97%, 98%, 99% or 100% complementarity.

"Repeat sequence" or "repetitive sequence" refers to non-coding tandemly repeated nucleotide sequences in the human genome including, e.g., repeat sequences from the alpha satellite, satellite 1, satellite 2, satellite 3, the beta satellite, the gamma satellite and telomeres. Repeat sequences are known in the art and are described in e.g., (Allshire et al., *Nucleic Acids Res* 17(12): 4611-27 (1989); Cho et al., *Nucleic Acids Res* 19(6): 1179-82 (1991); Fowler et al., *Nucleic Acids Res* 15(9): 3929 (1987); Haaf et al., *Cell* 70(4): 681-96 (1992); Lee et al., *Chromosoma* 109(6): 381-9 (2000); Maeda and Smithies, *Annu Rev Genet.* 20: 81-108 (1986); Meyne and Goodwin, *Chromosoma* 103(2): 99-103 (1994); Miklos (1985). Localized highly repetitive DNA sequences in vertebrate genomes. Molecular evolutionary genetics. I. J. R. Macintyre. NY, Plenum Publishing Corp.: 241-321 (1985); Tagarro et al., *Hum Genet.* 93(2): 125-8 (1994); Waye and Willard, *PNAS USA* 86(16): 6250-4 (1989); and Willard and Waye, *J Mol Evol* 25(3): 207-14 (1987). The repeat sequences are located at, e.g., the centromeric, pericentromeric, heterochromatic, and telomeric regions of chromosomes. Consensus repeat sequences are described in, e.g. Willard and Waye, *J Mol Evol* 25(3): 207-14 (1987) and Tagarro et al., *Hum Genet.* 93(2): 125-8 (1994). Vissel and Choo, *Nucleic Acids Res.* 15(16): 6751-6752 (1987), Cho et al., *Nucleic Acids Res* 19(6): 1179-82 (1991).

The term "chromosome-specific nucleic acid sequence," or "chromosome-specific nucleotide sequence," as used herein, refers to a nucleic acid sequence that is specific to a particular chromosome within the genome of a cell.

The term "probe" refers to an oligonucleotide that includes a target-binding region that is substantially complementary to a target sequence in a target nucleic acid and, thus, is capable of forming a hydrogen-bonded duplex with the target nucleic acid. Typically, the probe is a single-stranded probe, having one or more detectable labels to permit the detection of the probe following hybridization to its complementary target.

As used herein, "target-binding region" refers to a portion of an oligonucleotide probe that is capable of forming a hydrogen-bonded duplex with a complementary target nucleic acid.

The term "detectable label," as used herein, refers to a moiety that indicates the presence of a corresponding molecule (e.g., probe) to which it is bound.

An "indirect label" refers to a moiety, or ligand, that is detected using a labeled secondary agent, or ligand-binding partner, that specifically binds to the indirect label.

A "direct label" refers to a moiety that is detectable in the absence of a ligand-binding partner interaction.

The term "biological sample" refers to a material of biological origin (e.g., cells, tissues, organs, fluids).

A "linker," in the context of attachment of two molecules (whether monomeric or polymeric), means a molecule (whether monomeric or polymeric) that is interposed between and adjacent to the two molecules being attached. A "linker" can be used to attach, e.g., oligonucleotide probe sequence and a label (e.g., a detectable label). The linker can be a nucleotide linker (i.e., a sequence of the nucleic acid that is between and adjacent to the non-adjacent sequences) or a non-nucleotide linker.

The term "hybrid" refers to a double-stranded nucleic acid molecule formed by hydrogen bonding between complementary nucleotides.

The term "stringency" refers to hybridization conditions that affect the stability of hybrids, e.g., temperature, salt concentration, pH, formamide concentration, and the like. These conditions are empirically optimized to maximize specific binding, and minimize nonspecific binding, of a probe to a target nucleic acid.

The term "fluorophore" refers to a chemical group having fluorescence properties.

The term "optionally" means that the recited step (e.g., in the case of methods of the invention) or component (e.g., in the case of kits of the invention) may or may not be included.

Methods for Detecting a Target Nucleic Acid

The present invention provides, in one embodiment, a method of determining whether a target nucleic acid is present in a biological sample on a solid surface. In this embodiment, the method comprises the steps of: a) contacting the sample on the solid surface with a dry fibrous matrix, wherein labeled nucleic acid probes for detecting the target nucleic acid are embedded in or sorbed to the matrix, and wherein the labeled nucleic acid probes comprise nucleotide sequences that are substantially complementary to one or more different nucleotide sequences in the target nucleic acid; b) hydrating the matrix to release the probes from the matrix; c) incubating the sample with the probes under stringent conditions sufficient to permit specific hybridization of the probes to the target nucleic acid if present in the sample; d) washing the sample to remove unhybridized probes and non-specifically hybridized probes; and e) determining whether the target nucleic acid is present in the sample by determining whether the labeled nucleic acid probes have hybridized to the sample.

The biological sample is on a solid surface and can be affixed or attached to the surface. Suitable solid surfaces include, but are not limited to, a microscope slide (e.g., a glass slide, a plastic slide, a quartz slide), a coverslip, and a multi-wall (e.g., microtitre) plate. Preferably, the biological sample is affixed or attached to a glass slide. Suitable biological samples for the methods of the invention include, for example, chromosome preparations, cells (e.g., cultured cells), tissues, organs, blood, spinal fluid, lymph fluid, tears, saliva, sputum, urine, semen, amniotic fluid, hair, skin, and tumors (e.g., a biopsy). Preferably, the biological sample includes cells containing chromosomal DNA. Preferred cells include epithelial cells, sperm cells, oocytes, polar bodies, blastomeres and blastocysts. In a particular embodiment, the biological sample includes urothelial cells (e.g., human urothelial cells). Preferably, the biological sample is obtained from an animal (e.g., a non-human mammal, a human). In a particular embodiment, the biological sample is obtained from a human.

A biological sample can include, in one embodiment, a single target nucleic acid or, in alternative embodiments, multiple target nucleic acids (e.g., two or more distinct target nucleic acids). Target nucleic acids can be DNA or RNA and can include intragenic, intergenic and/or transgenic nucleotide sequences. Thus, target nucleic acids can be endogenous genomic nucleotide sequences or artificial or foreign (e.g., transgenic) nucleotide sequences. Typically, a target nucleic acid comprises a chromosome-specific nucleotide sequence. Exemplary chromosome-specific nucleotide sequences are shown in Table 1.

TABLE 1

Exemplary Chromosome-Specific Nucleic Acid Sequences.

| SEQ ID NO: | NAME | SEQUENCE (5'-3') |
|---|---|---|
| 1 | Y1 | CCAGTCGAATCCATTCGAGTACATACC |
| 2 | Y2 | CCTTTTGAATCCATTCCATTGGAGTCC |
| 3 | Y3 | ATTCATTGCATTCCGTTTCATGAAATTCGA |
| 4 | Y4 | CTGCATACAATTTCACTCCATTCGTTCCCA |
| 5 | Y5 | TCCATTGGAGTCAATTCCTTTCGACACCCA |
| 6 | Y6 | TTGATCCTATTTTATTAAATTGCATTCTAT |
| 7 | 2.1.1 | GTGCGCCCTCAACTAACAGTGTTGAAGCTT |
| 8 | 2.2.2 | GAAACGGGATTGTCTTCATATAAACTCTAG |
| 9 | 2.5.1 | GTATCTTCCAATAAAAGCTAGATAGAAGCA |
| 10 | 2.6.1 | ATGTCAGAAACTTTTTCATGATGTATCTAC |
| 11 | 2.7.3 | TATGTGTGATGTGCGCCCTCAACTAAGAGT |
| 12 | 2.8.4 | TCTCAGAAGCTTCATTGGGATGTTTCAATT |
| 13 | 2.10.1 | GGAATACGGTGATAAAGGAAATATCTTCCA |
| 14 | 4.3.2 | TCTTTGTGTTGTGTGTACTCATGTAACAGT |
| 15 | 4.6.2 | TTTCTGCCCTACCTGGAAGCGGACATTTCG |
| 16 | 4.7.5 | GGTTATCTTCATATAAAATCCAGACAGGAG |
| 17 | 4.10.2 | CGGCACTACCTGGAAGTGGATATTTCGAGC |
| 18 | 4.18.7 | TCTGCACTACCTGGAAGAGGCCATTTCGAG |
| 19 | 4.22.10 | CCTACGGGAGAAAGGAAATATCTTCAAAT |

Target nucleic acids can include unique or repetitive nucleotide sequences. Preferably, the target nucleic acid includes a repetitive genomic sequence, for example, a repeat sequence of a specific human chromosome (i.e., chromosome 1, 2, 3, 4, 5, 6, 7, 8, 9, 10, 11, 12, 13, 14, 15, 16, 17, 18, 19, 20, 21, 22, the X chromosome or the Y chromosome). Suitable repeat sequences include, but are not limited to, a centromeric repeat sequence, a pericentromeric repeat sequence, a heterochromatin repeat sequence, a telomeric repeat sequence, an alpha satellite repeat sequence, a beta satellite repeat sequence, a gamma satellite repeat sequence, and a satellite 1, 2, or 3 repeat sequence. In some embodiments, the target nucleic acid includes a target sequence of about 20 to about 50 contiguous nucleotides within a specific sequence (e.g., a specific repeat sequence).

Typically, the biological sample employed in the methods of the invention is a fixed sample (e.g., a fixed cell sample, a fixed tissue sample, a chromosome spread). A variety of suitable fixatives are known in the art and include, for example, acid acetone solutions, various aldehyde solutions (e.g., formaldehyde, paraformaldehyde, and glutaraldehyde) and acid alcohol solutions. Examples of specific fixatives for chromosomal preparations are discussed, for example, in Trask et al. (Science 230:1401-1402, 1985). The biological sample can be prepared (e.g., fixed) in solution, or on a solid support.

The biological sample can be optionally pretreated to make nucleic acids in the sample more accessible to probes. Such pretreatment can include, for example, treating a biological sample with one or more proteinases (e.g., proteinase K, trypsin, pepsin, collagenase) and/or mild acids (e.g., 0.02-0.2 N HCl, 25% to 75% acetic acid), treating a biological sample with RNase to remove residual RNA, detergent permeabilization, heat denaturation and aging of the sample. Other pretreatment steps include denaturing the sample chemically. In one embodiment, the biological sample is denatured in a non-alkaline denaturation buffer (e.g., 70% formamide) at an elevated temperature (e.g., 72° C.). In another embodiment, the biological sample is denatured in a solution comprising at least one base (e.g., NaOH) and at least one alcohol (e.g., ethanol) at room temperature. Preferably, the base/alcohol solution comprises about 0.07N base and about 70% ethanol.

According to the invention, the biological sample is contacted with a dry fibrous matrix containing nucleic acid probes. The dry fibrous matrix can be composed of a naturally-occurring fiber or a synthetic fiber. The fiber can be a woven fiber or a non-woven fiber. Exemplary fibers include, but are not limited to, glass fibers, wool fibers, and plant fibers. In a preferred embodiment, the fiber is a glass fiber. In another embodiment, the fibrous matrix comprises a cellulose-based material (e.g., a cellulose fiber). Suitable cellulose-based materials include, but are not limited to, cellulose, nitrocellulose, carboxymethylcellulose, rayon, and viscose.

In a particular embodiment, the dry fibrous matrix is a filter paper (e.g., a cellulose-based filter paper, a glass fiber filter paper). Suitable filter papers are available commercially, including, for example, Whatman™ cellulose and glass microfiber filter papers (GE Healthcare).

The dry fibrous matrix contains labeled nucleic acid probes for detecting a target nucleic acid. Preferably, the probes are chromosome-specific probes. The probes can be on, attached to, affixed to, deposited on, embedded in, or sorbed to the matrix. Methods of preparing fibrous matrices containing nucleic acids are known in the art.

In one embodiment, the nucleic acid probes are denatured after they are embedded in, or sorbed to, the matrix, prior to placing the matrix on the sample. For example, the fibrous matrix can be heated to a suitable temperature (e.g., 100° C.) to denature the probes after the probes have been deposited on the matrix. At the same time, the matrix is dried (e.g., dehydrated) to prevent the probes from renaturing. Once the matrix has been dried, the denatured probes cannot renature until the matrix is rehydrated.

Probes that are useful in the methods of the invention comprise a nucleotide sequence, also referred to as a target binding region, which is substantially complementary to a nucleotide sequence (e.g., a target sequence) in a target nucleic acid in the sample. Although generally desirable, a target binding region in a probe is not required to have 100% complementarity to the target nucleic acid. For example, in some embodiments, probes useful in the methods of the invention can comprise a nucleotide sequence that is at least about 70%, about 80%, about 90%, about 95% or about 99%, complementary to a nucleotide sequence in a target nucleic acid.

In a particular embodiment, the probes used in the methods of the present invention are oligonucleotide probes (e.g., single stranded DNA oligonucleotide probes). Typical oligonucleotide probes are linear and range in size from about 20 to about 100 nucleotides, preferably, about 30 to about 50 nucleotides. In a particular embodiment, the oligonucleotide probes are about 30 nucleotides in length.

Suitable probes for use in the methods of the invention include, but are not limited to, DNA probes, RNA probes, peptide nucleic acid (PNA) probes, locked nucleic acid (LNA) probes, morpholino probes, glycol nucleic acid (GNA) probes and threose nucleic acids (TNA) probes. Such probes can be chemically or biochemically modified and/or may contain non-natural or derivatized nucleotide bases. For example, a probe may contain modified nucleotides having modified bases (e.g., 5-methyl cytosine) and/or modified sugar groups (e.g., 2'O-methyl ribosyl, 2'O-methoxyethyl ribosyl, 2'-fluoro ribosyl, 2'-amino ribosyl). Although linear probes are preferred, useful probes can be circular or branched and/or include domains capable of forming stable secondary structures (e.g., stem-and-loop and loop-stem-loop hairpin structures).

Methods of producing probes useful in the methods of the invention are well known in the art and include, for example, biochemical, recombinant, synthetic (e.g., chemical synthesis) and semi-synthetic methods. In one embodiment, the oligonucleotide probes employed in the methods of the invention are produced by chemical synthesis. A synthetic oligonucleotide probe can be produced using known methods for nucleic acid synthesis (see, e.g., Glick and Pasternak, Molecular Biotechnology: Principles and Applications of Recombinant DNA (ASM Press 1998)). For example, solution or solid-phase techniques can be used. Synthesis procedures are typically automated and can include, for example, phosphoramidite, phosphite triester, H-phosphate, or phosphotriester methods.

Probes useful in the methods of the invention can further comprise one or more detectable labels. Labels suitable for use according to the present invention are known in the art and generally include any molecule that, by its chemical nature, and whether by direct or indirect means, provides an identifiable signal allowing detection of the probe. Thus, for example, probes may be labeled in a conventional manner, such as with specific reporter molecules, fluorophores, radioactive materials, or enzymes (e.g., peroxidases, phosphatases). In a particular embodiment, the probes employed in the methods of the invention include one or more fluorophores as detectable labels.

Detectable labels suitable for attachment to probes can be indirect labels or direct labels. Exemplary indirect labels include, e.g., haptens, biotin, or other specifically bindable ligands. For indirect labels, the ligand-binding partner typically has a direct label, or, alternatively, is also labeled indirectly. Examples of indirect labels that are haptens include dinitrophenol (DNP), digoxigenin, biotin, and various fluorophores or dyes (e.g., fluorescein, DY490, DY590, Alexa 405/Cascade blue, Alexa 488, Bodiby FL, Dansyl, Oregon Green, Lucifer Yellow, Tetramethylrhodamine/Rhodamine Red, and Texas Red). As an indirect label, a hapten is typically detected using an anti-hapten antibody as the ligand-binding partner. However, a hapten can also be detected using an alternative ligand-binding partner (e.g., in the case of biotin, anti-biotin antibodies or streptavidin, for example, can be used as the ligand-binding partner). Further, in certain embodiments, a hapten can also be detected directly (e.g., in the case of fluorescein, an anti-fluorescein antibody or direct detection of fluorescence can be used).

Exemplary "direct labels" include, but are not limited to, fluorophores (e.g., fluorescein, rhodamine, Texas Red, phycoerythrin, Cy3, Cy5, DY fluors (Dyomics GmbH, Jena, Germany) Alexa 532, Alexa 546, Alexa 568, or Alexa 594). Other direct labels can include, for example, radionuclides (e.g., 3H, 35S, 32P, 125I, and 14C), enzymes such as, e.g., alkaline phosphatase, horseradish peroxidase, or β-galactosidase, chromophores (e.g., phycobiliproteins), luminescers (e.g., chemiluminescers and bioluminescers), and lanthanide chelates (e.g., complexes of Eu3+ or Tb3+). In the case of fluorescent labels, fluorophores are not to be limited to single species organic molecules, but include inorganic molecules, multi-molecular mixtures of organic and/or inorganic molecules, crystals, heteropolymers, and the like. For example, CdSe-CdS core-shell nanocrystals enclosed in a silica shell can be easily derivatized for coupling to a biological molecule (Bruchez et al., *Science,* 281:2013-2016, 1998). Similarly, highly fluorescent quantum dots (zinc sulfide-capped cadmium selenide) have been covalently coupled to biomolecules for use in ultrasensitive biological detection (Warren and Nie, *Science,* 281: 2016-2018, 1998).

Probe labeling can be performed, e.g., during synthesis or, alternatively, post-synthetically, for example, using 5'-end labeling, which involves the enzymatic addition of a labeled nucleotide to the 5'-end of the probe using a terminal transferase. A single labeled nucleotide can be added by using a "chain terminating" nucleotide. Alternatively, non-terminating nucleotides can be used, resulting in multiple nucleotides being added to form a "tail." For synthesis labeling, labeled nucleotides (e.g., phosphoramidite nucleotides) can be incorporated into the probe during chemical synthesis. Labels can be added to the 5',3', or both ends of the probe (see, e.g., U.S. Pat. No. 5,082,830), or at base positions internal to the ODN.

Other methods for labeling nucleic acids utilize platinum-based labeling. Such methods include the Universal Linkage System (ULS, Kreatech Biotechnology B.V., Amsterdam, Netherlands). Platinum based labeling methods and their applications are described in, for example, U.S. Pat. Nos. 5,580,990, 5,714,327, and 6,825,330; International Patent Publication Nos. WO 92/01699, WO 96/35696, and WO 98/15546; Hernandez-Santoset et al., Anal. Chem. 77:2868-2874, 2005; Raap et al., BioTechniques 37:1-6, 2004; Heetebrij et al., ChemBioChem 4:573-583, 2003; Van de Rijke et al., Analytical Biochemistry 321:71-78, 2003; Gupta et al., Nucleic Acids Research 31:e13, 2003; Van Gijlswijk et al., Clinical Chemistry 48:1352-1359, 2002; Alers et al., Genes, Chromosomes & Cancer 25:301-305, 1999; Wiegant et al., Cytogenetics and Cell Genetics 87:7-52, 1999; Jelsma et al., Journal of NIH Research 5:82, 1994; Van Belkum et al., BioTechniques 16:148-153, 1994; and Van Belkum et al., Journal of Virological Methods 45:189-200, 1993.

Labeled nucleotide(s) can also be attached to a probe using a crosslinker or a spacer. Crosslinkers may be homobifunctional or heterobifunctional. Suitable homobifunctional crosslinkers include, e.g., amine reactive crosslinkers with NHS esters at each end (including, e.g., dithiobis(succinimidylproponate) (DSP); 3,3'-dithiobis(sulfosuccinimidylpropionate) (DTSSP); disuccinimidyl suberate (DSS); Bis(sulfosuccinimidyl)suberate (BS3); Ethylene glycolbis(succinimidylsuccinate) (EGS); Ethylene glycolbis(sulfosuccinimidylsuccinate) (SulfoEGS)); amine reactive crosslinkers with imidoesters at both ends (including, e.g., dimethyl adipimidate (DMA); dimethyl pimelimidate (DMP); dimethyl suberimidate (DMS); dimethyl 3,3'-dithiobispropionimidate (DTBP)); sulfhydryl reactive crosslinkers with dithiopyridyl groups at each end (including, e.g., 1,4-di-[3'-(2'-pyridyldithio)propionamido]butane (DPDPB)); sulfhydryl reactive crosslinkers with maleimide groups at each end (including, e.g., bismaleimidohexane (BMH)); carboxyl reactive crosslinkers with hydrazide groups at each end (including, e.g., adipic acid dihydrazide and carbonhydrazide); multi-group reactive crosslinkers with epoxide groups at each end (including, e.g., 1,2:3,4-diepoxybutane; 1,2:5,6-diepoxyhexane; Bis(2,3-epoxypropyl)ether; 1,4-(butanediol)diglycidyl ether). Suitable heterobifunctional crosslinkers include crosslinkers with an amine reactive end and a sulfhydryl-reactive end (including, e.g., N-Succinimidyl 3-(2-pyridyldithio)propionate (SPDP); long chain SPDP (SPDP); Sulfo-LC-SPDP; Succinimidyloxycarbonyl-α-methyl-α-(2-pyridyldithio)toluene (SMPT); Sulfo-LC-SMPT; Succinimidyl-4-(N-maleimidomethyl)cyclohexane (SMCC); Sulfo-SMCC; Succinimidyl 6-((iodoacetyl)amino)hexanoate (SIAX); Succinimidyl 6-(6-(((4-iodoacetyl)amino)hexanoyl)amino)hexanoate (SIAXX)); crosslinkers with a carbonyl-reactive end and a sulfhydryl reactive end (including, e.g., 4-(4-N-Maleimidophenyl)butyric acid hydrazide (MPBH); 4-(N-Maleimidomethyl)cyclohexane-1-carboxylhydrazide hydrochloride (M2C2H); 3-(2-Pyridyldithio)propinyl hydrazide (PDPH)); crosslinkers with an amine-reactive end and a photoreactive end (including, e.g., Sulfosuccinimidyl-2-(p-azidosalicylicylamido)ethyl-1,3'-dithiopropionate (SASD); Sulfosuccinimidyl 2-(7-azido-4-methylcoumarin-3-acetamide)ethyl-1,3'-dithiopropionate (SAED)); crosslinkers with a sulfhydryl-reactive end and a photoreactive end (including, e.g., N-[4-p-Azidosalicylamido)butyl]-3'-(2'pyridyldithio)propionamide (APDP)); crosslinkers with a carbonyl-reactive end and a photoreactive end (including, e.g., 4-(p-Azidosalicylamido)butlyamine (ASBA)). Suitable spacers include, 5' ODN modifications such as dNTP's; and amine-reactive spacers such as amino- or sulfo-phosphoramidites including, e.g., butylphosphoramidites, pentylphosphoramidites, hexylphosphoramidites, heptylphosphoramidites, octylphosphoramidites, non-ylphosphoramidites, decylphosphoramidites, undecylphosphoramidites, dodecylphosphoramidites, pentadecylphosphoramidites, octadecylphosphoramidites. Other suitable amine-reactive spacers include e.g., activated polyethylene glycol (PEG) such as (monomethoxy)n glycol, wherein n=3-18 unit repeats. Additional suitable crosslinkers and spacers are set forth in Herman. "Bioconjugate Chemistry". Academic Press. New York, N.Y. 1996.

In some embodiments, the fibrous matrix carries a plurality of labeled probes having specificity for different target nucleic acids. In such embodiments, each probe is at least substantially complementary to a particular target nucleic acid in the sample and comprises a detectable label that is distinguishable from the detectable labels present on other probes that have specificity for other target nucleic acids in the sample. For example, each probe can comprise a fluorophore having a spectrally distinguishable emission wavelength. Suitable fluorophores for use in the kits of the invention having a plurality of different labeled probes include, e.g., Alexa 488 (excitation maximum at 492 nm and emission maximum at 520 nm) and Alexa 546 (excitation maximum at 555 nm and emission maximum at 570 nm)).

In other embodiments, the dry fibrous matrix includes one or more additional reagents that are embedded in or sorbed to the matrix. Such additional reagents include, for example, salmon sperm DNA, a blocking reagent (e.g., milk (e.g., skim milk), albumin, caseine) and an antimicrobial agent (e.g., sodium azide, thimerasol), or a combination thereof.

According to the invention, the fibrous matrix is hydrated to release the probes from the matrix prior to hybridizing the probes to target nucleic acids that may be present in the sample. The fibrous matrix can be hydrated immediately before or after the matrix is placed in contact with the biological sample. In one embodiment, the fibrous matrix is hydrated by applying one or more drops of a hydration buffer to the matrix. In a particular embodiment, the hydration buffer comprises a denaturing agent (e.g., formamide, NaOH).

In a particular embodiment, the hydration buffer comprises formamide, dextran sulfate and salt (e.g., saline sodium citrate (SSC)). Hydration buffers comprising formamide or other desestabilizing molecules, such as, for example, ethylene carbonate, DMSO) are particularly useful when the hybridization will be performed at an elevated temperature (e.g., 37-45° C.). Suitable concentrations of formamide in the hydration buffer include, for example, concentrations in the range of about 20% to about 90% by volume, e.g., about 60%, about 70%, or about 80% by volume. Suitable concentrations of dextran sulfate in the hydration buffer include, for example, about 3% to about 20% by volume. The concentration of total salt in the hydration buffer is preferably in the range of about 0.03M to about 0.09M. For example, concentrations of SSC in the hydration buffer can be, for example, in the range of about 0.1× to about 4.0×. Preferably, the hydration buffer comprises about 30% formamide, about 10% to about 20% dextran sulfate and about 2×SSC.

In another embodiment, the hydration buffer comprises a base (e.g., NaOH) and has a pH in the range of about 10 to about 13. Such basic hydration buffers are particularly useful when the hybridization will be performed at room temperature. Suitable bases for use in the hydration buffer include, without limitation, potassium hydroxide, barium hydroxide, caesium hydroxide, sodium hydroxide, strontium hydroxide, calcium hydroxide, lithium hydroxide, rubidium hydroxide, magnesium hydroxide, butyl lithium, lithium diisopropylamide, lithium diethylamide, sodium amide, sodium hydride, lithium bis(trimethylsilyl)amide, sodium carbonate and ammonia, or a combination thereof. Preferably, the base is an alkali base. More preferably, the base is sodium hydroxide. Suitable concentrations of base for the hydration buffer are typically in the range of about 0.03 normal (N) to about 0.17N, for example, about 0.05N, about 0.06N, about 0.07N, about 0.08N, about 0.09N or about 0.1N. In a particular embodiment, the solution comprises about 0.07N NaOH, which is equivalent to 0.07M NaOH.

In a particular embodiment, the probes are denatured after the matrix has been placed on the sample and hydrated (e.g., by heating the probes, matrix and sample to a temperature of about 75° C. for 5 minutes).

The methods of the invention further comprise the step of incubating the sample with the probes under stringent conditions sufficient to permit specific hybridization of the probes to the target nucleic acid if present in the sample. Generally, hybridization is performed under conditions (e.g., temperature, incubation time, salt concentration, etc.) sufficient for a probe to hybridize with a complementary target nucleic acid in a biological sample. Suitable hybridization buffers and conditions for in situ hybridization techniques are generally known in the art. (See, e.g., Sambrook and Russell, supra; Ausubel et al., supra. See also Tijssen, Laboratory Techniques in Biochemistry and Molecular Biology, Vol. 24: Hybridization with Nucleic Acid Probes (Elsevier, NY 1993)). For example, a hybridization buffer comprising formamide, dextran sulfate and saline sodium citrate (SSC) can be employed in the methods of the invention. Suitable concentrations of formamide in the hybridization buffer include, for example, concentrations in the range of about 20% to about 90% by volume, e.g., about 60%, about 70%, or about 80% by volume. Suitable concentrations of dextran sulfate in a hybridization buffer include, for example, about 3% to about 20%. Suitable concentrations of SSC in a hybridization buffer include, for example, about 0.1× to about 4.0×. The concentration of total salt in the hybridization buffer is preferably in the range of about 0.03M to about 0.09M. In a particular embodiment, the hydration buffer employed to hydrate the fibrous matrix is also used as the hybridization buffer.

Optimal hybridization conditions for a given target sequence and its complementary probe will depend upon several factors such as salt concentration, incubation time, and probe concentration, composition, and length, as will be appreciated by those of ordinary skill in the art. Based on these and other known factors, suitable binding conditions can be readily determined by one of ordinary skill in the art and, if necessary, optimized for use in accordance with the present methods. Typically, hybridization is carried out under stringent conditions that allow specific binding of substantially complementary nucleotide sequences. Stringency can be increased or decreased to specifically detect target nucleic acids having 100% complementarity or to detect related nucleotide sequences having less than 100% complementarity (e.g., about 70% complementarity, about 80% complementarity, about 90% complementarity). Factors such as the length and nature (DNA, RNA, base composition) of the probe sequence, nature of the target nucleotide sequence (DNA, RNA, base composition, presence in solution or immobilization) and the concentration of salts and other components in the hybridization buffer (e.g., the concentration of formamide, dextran sulfate, polyethylene glycol and/or salt) in the hybridization buffer/solution can be varied to generate conditions of either low, medium, or high stringency. These conditions can be varied based on nucleotide base composition and length and circumstances of use, either empirically or based on formulas for determining such variation (see, e.g., Sambrook et al., supra; Ausubel et al., supra). Preferred hybridization conditions include hybridizing at 37° C. for 5 to 10 minutes in a hybridization buffer comprising 2×SSC, 30% formamide, 10%-20% dextran sulfate. Other preferred hybridization conditions hybridizing at room temperature in a hybridization buffer comprising 6 mM NaOH, 30% formamide, 20% dextran sulfate for 5 to 10 minutes.

In one embodiment, the hybridization is performed at an elevated temperature (e.g., 37° C.). In an alternative embodiment, the hybridization is performed at room temperature.

According to the invention, the sample is washed after the hybridization step to remove unhybridized probes or non-specifically hybridized probes. Washes are performed in a solution of appropriate stringency to remove unbound and/or non-specifically bound probes. An appropriate stringency can be determined by washing the sample in successively higher stringency solutions and reading the signal intensity between each wash. Analysis of the data sets in this manner can reveal a wash stringency above which the hybridization pattern is not appreciably altered and which provides adequate signal for the particular probes of interest.

Suitable wash buffers for in situ hybridization methods are generally known in the art (See, e.g., Sambrook and Russell, supra; Ausubel et al., supra. See also Tijssen, Laboratory Techniques in Biochemistry and Molecular Biology, Vol. 24: Hybridization with Nucleic Acid Probes (Elsevier, NY 1993)). Wash buffers typically include, for example, one or more salts (e.g., sodium salts, lithium salts, potassium salts) and one or more detergents (e.g., an ionic detergent, a non-ionic detergent). Suitable detergents for a wash buffer include, but are not limited to, sodium dodecyl sulfate (SDS), Triton® X-100, Tween® 20, NP-40, or Igepal CA-630. Preferably, the wash buffer comprises one or more salts (e.g., sodium citrate) having a total concentration of about 0.03M to about 0.09M and about 0.1% SDS. In a particular embodiment, the wash buffer comprises 1.864 mM NaOH and 2×SSC.

The number of washes and duration of each wash can be readily determined by one of ordinary skill in the art. Exemplary wash conditions for the isothermal methods of the invention include, for example, an initial post-hybridization wash in 2×SSC for 5 min. at room temperature (e.g, about 21° C.) followed by one or more additional washes in 0.03M to 0.09M monovalent salt (e.g., SSC) and 0.1% SDS at room temperature for at least about 2 minutes per wash, preferably, in the range of about 2 minutes to about 5 minutes per wash.

After the sample has been subjected to post-hybridization washes, chromosomal DNA in the sample is preferably counter-stained with a spectrally distinguishable DNA specific stain such as, for example, 4',6-diamidino-2-phenylindole (DAPI), propidium iodide (PI) or a Hoechst reagent/dye and mounted using an antifade reagent. The DNA stain can be added directly to the antifade reagent or can be incubated with the sample, drained and rinsed before the antifade reagent is added. Reagents and techniques for counterstaining and mounting samples are generally known in the art.

The in situ hybridization methods of the invention further include detecting one or more target nucleic acids in the sample. The target nucleic acid is detected by detecting a labeled probe that has hybridized to the target nucleic acid. Detection of the probe label can be accomplished using an approach that is suitable for the particular label, which can be readily determine by those of ordinary skill in the art. For example, fluorophore labels can be detected by detecting the emission wavelength of the particular fluorophore used. Typical methods for detecting fluorescent signals include, e.g., spectrofluorimetry, epifluorescence microscopy, confocal microscopy, and flow cytometry analysis. Fluorescent labels are generally preferred for detection of low levels of target because they provide a very strong signal with low background. Furthermore, fluorescent labels are optically detectable at high resolution and sensitivity through a quick scanning procedure, and different hybridization probes having fluorophores with different emission wavelengths (e.g., fluorescein and rhodamine) can be used for a single sample to detect multiple target nucleic acids.

In the particular case of fluorescence in situ hybridization (FISH) procedures, which utilize fluorescent probes, a variety of different optical analyses can be utilized to detect hybridization complexes. Spectral detection methods are discussed, for example, in U.S. Pat. No. 5,719,024; Schroeck et al. (Science 273:494-497, 1996); and Speicher et al. (Nature Genetics 12:368-375, 1996). Further guidance regarding general FISH procedures are discussed, for example, in Gall and Pardue (Methods in Enzymology 21:470-480, 1981); Henderson (International Review of Cytology 76:1-46, 1982); and Angerer et al. in Genetic Engineering: Principles and Methods (Setlow and Hollaender eds., Plenum Press, New York, 1985).

Detection of indirect labels typically involves detection of a binding partner, or secondary agent. For example, indirect labels such as biotin and other haptens (e.g., digoxigenin (DIG), DNP, or fluorescein) can be detected via an interaction with streptavidin (i.e., in the case of biotin) or an antibody as the secondary agent. Following binding of the probe and target, the target-probe complex can be detected by using, e.g., directly labeled streptavidin or antibody. Alternatively, unlabeled secondary agents can be used with a directly labeled "tertiary" agent that specifically binds to the secondary agent (e.g., unlabeled anti-DIG antibody can be used, which can be detected with a labeled second antibody specific for the species and class of the primary antibody). The label for the secondary agent is typically a non-isotopic label, although radioisotopic labels can be used. Typical non-isotopic labels include, e.g., enzymes and fluorophores, which can be conjugated to the secondary or tertiary agent. Enzymes commonly used in DNA diagnostics include, for example, horseradish peroxidase and alkaline phosphatase.

Detection of enzyme labels can be accomplished, for example, by detecting color or dye deposition (e.g., p-nitrophenyl phosphate or 5-bromo-4-chloro-3-indolyl phosphate/ nitroblue tetrazolium for alkaline phosphatase and 3,3'-diaminobenzidine-NiCl2 for horseradish peroxidase), fluorescence (e.g., 4-methyl umbelliferyl phosphate for alkaline phosphatase) or chemiluminescence (e.g., the alkaline phosphatase dioxetane substrates LumiPhos 530 from Lumigen Inc., Detroit Mich. or AMPPD and CSPD from Tropix, Inc.), depending on the type of enzymatic label employed. Chemiluminescent detection can be carried out with X-ray or Polaroid film or by using single photon counting luminometers (e.g., for alkaline phosphatase labeled probes).

In certain embodiments, digital enhancement or integration is used to detect a signal from a label on a probe. For example, detection of the label can include the use of microscopic imaging using a CCD camera mounted onto the eyepiece tube of a microscope (e.g., a binocular, monocular, or stereo microscope). In some embodiments, detection of the label is accomplished using image scanning microscopy. For example, recent advances in computerized image scanning microscopy have significantly increased the ability to detect rare cells using fluorescence microscopy, permitting detection of 1 positive cell in an environment of $\sim 6 \times 10^5$ negative cells (see, e.g., Mehes et al., Cytometry 42:357-362, 2000). Advanced image scanning software has been developed that can not only detect multiple colors but also fused or co-localized signals useful for, e.g., detection of translocations on the DNA level (MetaSystems Group, Inc.) Scanning speed typically depends on the number of parameters utilized for reliable detection of single positive cells. Image scanning also allows for images of the cells scored positive to be manually examined for confirmation. Advanced image scanning software for automated, slide-based analysis has been developed that can not only detect multiple colors but also fused or co-localized signals useful for, e.g., detection of translocations on the DNA level (MetaSystems Group, Inc.) Scanning speed typically depends on the number of parameters utilized for reliable detection of single positive cells. Automated slide-based scanning systems are particularly amenable to high throughput assays.

In one embodiment, scanning slide microscopy, e.g., employing a MetaCyte Automated Bio-Imaging System (Meta System Group, Inc.), is used. This system consists of the following components: 1) Carl Zeiss Axio Plan 2 MOT fluorescence microscope, 2) scanning 8-position stage, 3) PC Pentium III Processor, 4) Jai camera, 5) camera interface, 6) stage control, 7) trackball and mouse, and 8) printer. The focus analysis begins with a slide set-up loaded onto the microscope. The slide is scanned as the stage is moved and the image is captured. Following scanning of the entire slide, a gallery is created. Based on the criterion set up for positive or negative, the image analysis either results in a positive or negative signal. If negative, the slide is rescanned for rare event analyses. If positive, there is a filter change for the appropriate fluorescent signal and 5-7 planes are captured and analyzed. There is walk away/overnight operation for 8 slides (standard or 100 slides with optional tray changer). Adaptive detection algorithms and automatic exposure control function compensate for non-uniform staining conditions. Several markers can be detected simultaneously. The standard light source covers a wide spectrum from UV to IR. Scanning speed up to 1,000 cells per second can be used for rare cell detection if cellular fluorescent intensity allows detection in $\frac{1}{1,000}$ sec. For strong signals, a lower magnification can be used to increase scanning speed.

Alternatively, detection of the probe can be performed in the absence of digital enhancement or integration.

Methods of Enumerating Chromosomes

In a particular embodiment, the invention relates to a method of enumerating chromosomes in a sample of cells immobilized on a slide. Preferably, the cells are epithelial cells (e.g., urothelial cells, peripheral blood cells), sperm cells, oocytes, polar bodies, blastomeres, blastocysts, or a combination thereof. In one embodiment the cells are affixed to a glass microscope slide.

The method comprises overlaying the sample on the slide with a dry fibrous matrix comprising a glass fiber, wherein fluorescently-labeled synthetic DNA oligonucleotide probes for detecting one or more target chromosomal sequences in the sample are embedded in or sorbed to the matrix. The oligonucleotide probes comprise nucleotide sequences that are substantially complementary to nucleotide sequences in the one or more target chromosomal sequences. Preferably, the oligonucleotide probes are chromosome-specific probes. In one embodiment, the oligonucleotide probes are in the range of about 20 to about 50 nucleotides in length, more preferably about 30 nucleotides in length.

The method further comprises hydrating the matrix with a hydration buffer to release the probes from the matrix. In a particular embodiment, the hydration buffer comprises formamide, dextran sulfate and salt (e.g., saline sodium citrate (SSC)). Preferably, the hydration buffer comprises about 30% formamide, about 10% to about 20% dextran sulfate and about 2×SSC. In another embodiment, the hydration buffer comprises a base (e.g., NaOH) and has a pH in the range of about 10 to about 13.

The method further comprises incubating the sample with the probes under stringent conditions sufficient to permit specific hybridization of the probes to the target chromosomal sequences, if present in the sample. Suitable conditions for specific hybridization of the probes to the target chromosomal sequences can be determined by a person of ordinary skill in the art and include, for example, hybridizing at 37° C. for 5-10 minutes in a hybridization buffer comprising 2×SSC, 30% formamide and 10-20% dextran sulfate. Other preferred hybridization conditions hybridizing at room temperature in a hybridization buffer comprising 6 mM NaOH, 30% formamide and 20% dextran sulfate for 5-10 minutes. Preferably, the hydration buffer employed to hydrate the fibrous matrix is also used as the hybridization buffer. In one embodiment, the hybridization is performed at an elevated temperature (e.g., 37° C.). In an alternative embodiment, the hybridization is performed at room temperature.

The method of enumerating chromosomes further comprises the steps of washing the sample to remove unhybridized probes and non specifically hybridized probes and enumerating chromosomes having the target chromosomal sequences in the sample by detecting labeled nucleic acid probes that have hybridized to the target chromosomal sequences in the sample. Washes and detection may be performed as described herein above for the method of determining whether a target nucleic acid is present in a biological sample.

Kits for Detecting Target Nucleic Acids

In another embodiment, the invention relates to a kit for detecting a target nucleic acid in a sample. The kit includes a dry fibrous matrix comprising labeled nucleic acid probes for detecting a target nucleic acid and a hydration buffer for releasing the probes from the matrix. The labeled nucleic acid probes are embedded in or sorbed to the matrix and comprise nucleotide sequences that are substantially complementary to one or more nucleotide sequences in the target nucleic acid.

The dry fibrous matrix can be composed of a naturally-occurring fiber or a synthetic fiber. The fiber can be a woven fiber or a non-woven fiber. Exemplary fibers include, but are not limited to, glass fibers, wool fibers, and plant fibers. In a preferred embodiment, the fiber is a glass fiber. In another embodiment, the fibrous matrix comprises a cellulose-based material (e.g., a cellulose fiber). Suitable cellulose-based materials include, but are not limited to, cellulose, nitrocellulose, carboxymethylcellulose, rayon, and viscose.

In a particular embodiment, the dry fibrous matrix is a filter paper (e.g., a cellulose-based filter paper, a glass fiber filter paper). Suitable filter papers are available commercially, including, for example, Whatman™ cellulose and glass microfiber filter papers (GE Healthcare).

The dry fibrous matrix includes nucleic acid (e.g., DNA, RNA) probes that comprise a target binding region that is substantially complementary to a target sequence in a target nucleic acid. The nucleic acid probes are embedded in or sorbed to the dry fibrous matrix. Preferably, the probes are chromosome-specific probes.

Suitable probes for use in the methods of the invention include, but are not limited to, DNA probes, RNA probes, peptide nucleic acid (PNA) probes, locked nucleic acid (LNA) probes, morpholino probes, glycol nucleic acid (GNA) probes and threose nucleic acids (TNA) probes. Such probes can be chemically or biochemically modified and/or may contain non-natural or derivatized nucleotide bases. For example, a probe may contain modified nucleotides having modified bases (e.g., 5-methyl cytosine) and/or modified sugar groups (e.g., 2'O-methyl ribosyl, 2'O-methoxyethyl ribosyl, 2'-fluoro ribosyl, 2'-amino ribosyl). Although linear probes are preferred, useful probes can be circular or branched and/or include domains capable of forming stable secondary structures (e.g., stem-and-loop and loop-stem-loop hairpin structures).

Preferably, the probes are oligonucleotide probes. Suitable oligonucleotide probes are typically about 20 to about 100 nucleotides in length, preferably about 20 to about 50 nucleotides in length, and more preferably about 30 nucleotides in length. Preferably, the oligonucleotide probes in the kits of the invention are single-stranded DNA probes.

In certain embodiments, the probes in the kits of the invention are labeled (e.g., comprise one or more detectable labels). Exemplary detectable labels for probes are described herein. Preferably, the oligonucleotide probes in the kits of the invention comprise one or more fluorophores (e.g., fluorescein, rhodamine, Texas Red, phycoerythrin, Cy3, Cy5, Alexa 532, Alexa 546, Alexa 568, or Alexa 594).

In some embodiments, the fibrous matrix carries a plurality of different labeled probes. In such embodiments, each probe is specific for a particular target nucleic acid and comprises a detectable label that is distinguishable from the detectable labels present on other probes that have specificity for other target nucleic acids. For example, each probe can comprise a fluorophore having a spectrally distinguishable emission wavelength. Suitable fluorophores for use in the kits of the invention having a plurality of different labeled probes include, e.g., Alexa 488 (excitation maximum at 492 nm and emission maximum at 520 nm) and Alexa 546 (excitation maximum at 555 nm and emission maximum at 570 nm)).

In some embodiments, the dry fibrous matrix includes one or more additional reagents that are embedded in or sorbed to the matrix. Such additional reagents include, for example, salmon sperm DNA, a blocking reagent (e.g., milk (e.g., skim milk), albumin, caseine) and an antimicrobial agent (e.g., sodium azide, thimerasol), or a combination thereof.

The kits of the invention also include a hydration buffer. In some embodiments, the hydration buffer also functions as a hybridization buffer. In a particular embodiment, the hydration buffer comprises formamide, dextran sulfate and salt (e.g., saline sodium citrate (SSC)). Suitable concentrations of formamide in the hydration buffer include, for example, concentrations in the range of about 20% to about 90% by volume, e.g., about 60%, about 70%, or about 80% by volume. Suitable concentrations of dextran sulfate in the hydration buffer include, for example, about 3% to about 20%. The concentration of total salt in the hydration buffer is preferably in the range of about 0.03M to about 0.09M. For example, concentrations of SSC in the hydration buffer can be, for example, in the range of about 0.1× to about 4.0×. Preferably, the hydration buffer comprises about 30% formamide, about 10% to about 20% dextran sulfate and 2×SSC.

In another embodiment, the hydration buffer comprises a base (e.g., NaOH) and has a pH in the range of about 10 to about 13. A hydration buffer comprising a base is particularly useful when the hybridization will be performed at room temperature. Suitable bases for use in the hydration buffer include, without limitation, potassium hydroxide, barium hydroxide, caesium hydroxide, sodium hydroxide, strontium hydroxide, calcium hydroxide, lithium hydroxide, rubidium hydroxide, magnesium hydroxide, butyl lithium, lithium diisopropylamide, lithium diethylamide, sodium amide, sodium hydride, lithium bis(trimethylsilyl)amide, sodium carbonate and ammonia, or a combination thereof. Preferably, the base is an alkali base. More preferably, the base is sodium hydroxide. Suitable concentrations of base for the hydration buffer are typically in the range of about 0.03 normal (N) to about 0.17N, for example, about 0.05N, about 0.06N, about 0.07N, about 0.08N, about 0.09N or about 0.1N. In a particular embodiment, the solution comprises about 0.07N NaOH, which is equivalent to 0.07M NaOH.

In some embodiments, the kits may include additional, optional components, such as, for example, a denaturation buffer (e.g., a buffer comprising NaOH and an alcohol), a wash buffer, a secondary detection reagent, a stain for chromosomal DNA, an antifade reagent, instructions, protocols or a combination thereof. Typically, the kits are compartmentalized for ease of use and may include one or more containers with reagents. In one embodiment, all of the kit components are packaged together. Alternatively, one or more individual components of the kit may be provided in a separate package from the other kits components (e.g., the hydration buffer may be packaged separately from the fibrous matrix).

In some embodiments, the kits of the invention include a denaturation buffer that comprises a base (e.g., NaOH) and an alcohol. The denaturation buffer preferably includes about 0.03N to about 0.17N base, for example, about 0.05N, about 0.06N, about 0.07N, about 0.08N, about 0.09N or about 0.1N base. Preferably, the denaturation buffer comprises about 0.07N NaOH (i.e., 0.07M NaOH). Exemplary bases for use in the denaturation buffer include, for example, potassium hydroxide, barium hydroxide, caesium hydroxide, sodium hydroxide, strontium hydroxide, calcium hydroxide, lithium hydroxide, rubidium hydroxide, magnesium hydroxide, butyl lithium, lithium diisopropylamide, lithium diethylamide, sodium amide, sodium hydride, lithium bis(trimethylsilyl) amide, sodium carbonate and ammonia, or a combination thereof. Preferably, the base is an alkali base. More preferably, the base is sodium hydroxide. The denaturation buffer further includes at least one alcohol at a concentration of about 50% to about 90% by volume, for example about 60%, about 70% or about 80% by volume. Preferably, the alcohol is present at a concentration of about 70% by volume. Exemplary alcohols for use in the denaturation buffer include, for example, ethanol, methanol, propanol, butanol, pentanol and isoamyl alcohol, among others, or mixtures thereof. In a particular embodiment, the denaturation buffer comprises about 70% ethanol.

The kits of the invention may optionally include one or more wash buffers. Typically, the one or more wash buffers each comprise one or more salts (e.g., sodium salts, lithium salts or potassium salts) at a final concentration of about 0.03M to about 0.09M. In a particular embodiment, the wash buffer includes sodium citrate and sodium chloride. The wash buffers may further comprise a detergent including, but not limited to, sodium dodecyl sulfate (SDS). Suitable concentrations of SDS in the wash buffers are typically in the range of about 0.01% to about 1.0% SDS, preferably about 0.1% SDS. In addition, the wash buffers in the kits of the invention may optionally include formamide. In one embodiment the kit includes a wash buffer comprising 1.864 mM NaOH and 2×SSC.

Optionally, one or more reagent(s) for detecting labeled probes can be included in the kits of the invention. Such reagents or other elements recognized by the skilled artisan for use in a detection assay corresponding to the type of label on the probe. In one embodiment, the kit includes a secondary agent for detecting an indirect label on a probe (e.g., streptavidin labeled with a fluorophore).

A description of example embodiments of the invention follows.

Example

An In Situ Hybridization Method Performed Using Nucleic Acids Probes on a Fibrous Matrix Materials and Methods:
Preparation of a Composition Comprising Probes on a Fibrous Matrix Qualitative 1 (cellulose) and GF/A (fiberglass) Whatman filter disks were cut using a ½" hole puncher. A mixture of undiluted oligonucleotide probes specific for chromosomes 3, 6, 7 and 20 were deposited in a volume of 6-9 µL in the center of each type of disk. The disks were heated in an oven for 30 minutes at 60° C. The disks were stored at room temperature away from light.

Detection of Target Nucleic Acids in Biological Sample Comprising Epithelial Cells Following In Situ Hybridization Cytogenetic slides from peripheral blood were denatured for 10 minutes at room temperature with IsoThermal Denaturing Solution (Cellay, Inc., Cambridge, Mass.), then dehydrated in 85% and 100% alcohol for 1 minute each, and air dried. Paper disks with embedded probes were prepared as described above and placed over cells in the desired hybridization area of each slide. Hybridizations were carried out either at 37° C. with non-embedded probes in hybridization solution (10% dextran, 30% formamide, 2×SSC) under a coverslip or at room temperature with probes embedded on filter paper disks that were hydrated in a hybridization buffer of 20% dextran, 30% formamide, 6.0 mM NaOH. For the room temperature method, an appropriate volume of hybridization buffer diluted in water was added using a Pasteur pipette to the top of each paper disk. The slides were then either heated at 37° C. for 10 minutes or left at room temperature for 10 minutes. Following hybridization, the slides were washed in 2×SSC under agitation for 5 minutes at room temperature to remove the disks and then were washed in IsoThermal Washing Solution (Cellay, Inc., Cambridge, Mass.) for 5 minutes at room temperature hybridization to remove unhybridized and non-specifically hybridized probes. The slides were rinsed briefly in 2×SSC and dried before mounting with anti-fade reagent, DAPI and a cover slip. Mounted slides were placed in a slide holder for at least 10 minutes before they were analyzed.

Statistics

After measuring the signal-to-noise ratio for each fluor, the signal-to-noise ratio was averaged and the Standard error of the mean at 95% confidence was calculated as follows:

$$\text{Standard error of the mean} = z\frac{SD}{\sqrt{n}}$$

where z=1.96 for 95% confidence, SD=standard deviation and n=number of cells (200).

Results

Figure 1B:
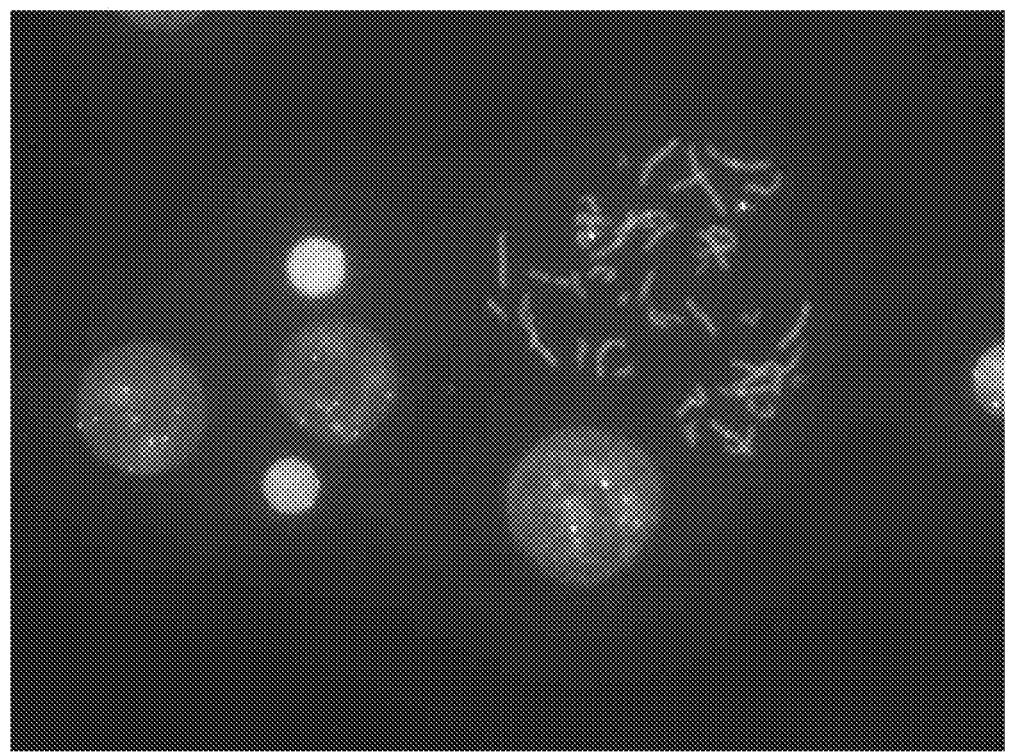
Figure 2:
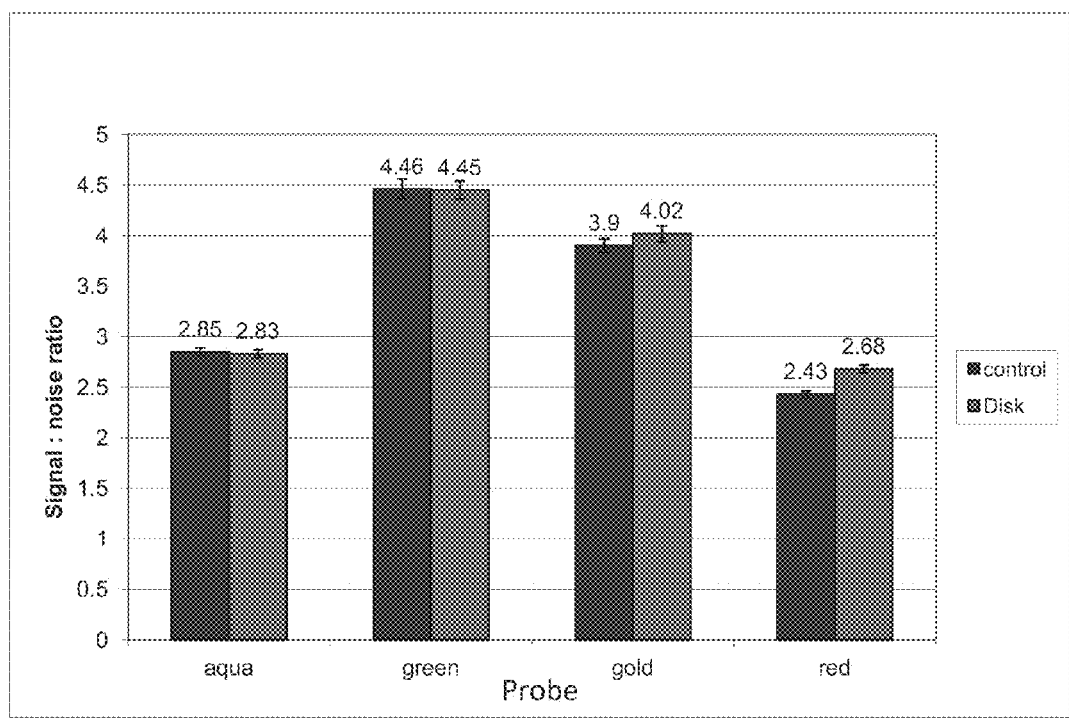
FIG. 2 is a bar graph showing signal-to-noise ratios obtained for an OligoFISH probe panel for chromosomes 3 (red), 6 (green), 7 (aqua) and 20 (gold) using either a standard in situ hybridization procedure involving an elevated temperature hybridization step and non-embedded probes under a coverslip (blue, control) or an in situ hybridization procedure involving a room temperature hybridization step and probes embedded on filter paper disks (green, Disks). Error bars are standard error of the mean.

Using the procedures described above, a panel of chromosome-specific probes embedded on filter paper disks was successfully used in an in situ hybridization procedure for the detection of chromosome-specific target nucleic acids in human peripheral blood cells (FIGS. 1A and 1B). These methods yielded similar results when the hybridizations were performed at an elevated temperature (37° C.) with non-embedded probes or at room temperature using probes embedded on filter paper disks (FIG. 2; compare elevated temperature (blue, control) to room temperature (green, Disk)).

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of determining whether a target nucleic acid is present in a biological sample on a solid surface, comprising the steps of:
   a) contacting the sample on the solid surface with a dry fibrous matrix and laying the dry fibrous matrix on the surface, wherein labeled nucleic acid probes for detecting the target nucleic acid are embedded in or sorbed to the matrix, and wherein the labeled nucleic acid probes comprise nucleotide sequences that are substantially complementary to one or more different nucleotide sequences in the target nucleic acid;
   b) hydrating the matrix on the surface in an aqueous hydration solution after step a) thereby releasing the probes from the matrix;
   c) incubating the sample on the surface with the probes under stringent conditions sufficient to permit specific hybridization of the probes to the target nucleic acid if the target nucleic acid is present in the sample;
   d) washing the surface to remove the probes which are unhybridized and non-specifically hybridized; and
   e) determining whether the target nucleic acid is present in the sample by determining whether the labeled nucleic acid probes have hybridized to the target nucleic acid.

2. The method of claim 1, wherein the fibrous matrix comprises a glass fiber, a wool fiber, a synthetic fiber or a plant fiber.

3. The method of claim 1, wherein the fibrous matrix comprises a cellulose-based material.

4. The method of claim 3, wherein the cellulose-based material is selected from the group consisting of cellulose, nitrocellulose, carboxymethylcellulose, rayon, and viscose.

5. The method of claim 1, wherein one or more additional reagents selected from the group consisting of salmon sperm DNA, a blocking reagent and an antimicrobial agent, or a combination thereof are embedded in or sorbed to the matrix.

6. The method of claim 1, wherein the aqueous hydration solution is an aqueous hybridization buffer comprising about 30% formamide, about 10% to about 20% dextran sulfate and 2×SSC solution.

7. The method of claim 1, wherein the labeled nucleic acid probes are DNA oligonucleotide probes.

8. The method of claim 7, wherein the DNA oligonucleotide probes have a length of about 20 to about 50 nucleotides.

9. The method of claim 8, wherein the DNA oligonucleotide probes have a length of about 30 nucleotides.

10. The method of claim 1, wherein the labeled nucleic acid probes are synthetically produced and comprise at least one fluorescent label.

11. The method of claim 1, wherein the biological sample is attached to or affixed to the solid surface.

12. The method of claim 1, wherein the biological sample comprises cells selected from the group consisting of epithelial cells, sperm cells, oocytes, polar bodies, blastomeres and blastocysts, or a combination thereof.

13. The method of claim 1, wherein the biological sample comprises epithelial cells, wherein the epithelial cells are selected from the group consisting of urothelial cells and peripheral blood cells, or a combination thereof.

14. The method of claim 1, wherein step c) of the method is performed at a temperature in the range of about 19 degrees Celsius to about 25 degrees Celsius.

15. The method of claim 14, wherein the aqueous hydration solution is a hybridization buffer comprising about 1.0-5.0 mM NaOH and having a pH in the range of about 10 to about 13.

16. The method of claim 1, wherein the biological sample is immobilized on the solid surface, wherein the solid surface comprises a glass slide.

17. The method of claim 1, wherein the hydration solution comprises formamide, ethylene carbonate or dimethylsulfoxide, or a combination thereof.

18. The method of claim 17, wherein the hydration solution comprises formamide.

19. The method of claim 18, wherein the formamide in the hydration solution has a concentration of about 20% to about 90% by volume.

20. The method of claim 19, wherein the formamide in the hydration solution has a concentration of about 30% by volume.

21. The method of claim 17, wherein the hydration solution further comprises dextran sulfate and saline sodium citrate.

22. The method of claim 1, wherein the hydration solution comprises a base and has a pH in the range of about 10 to about 13.

23. The method of claim 22, wherein the base comprises an alkali metal selected from the group consisting of Li, Na, K, Rb and Cs.

24. The method of claim 23, wherein the base is NaOH.

25. The method of claim 24, wherein the NaOH in the hydration solution has a concentration of about 0.03 M to about 0.17 M.

26. The method of claim 25, wherein the NaOH in the hydration solution has a concentration of about 0.07 M.

* * * * *